United States Patent [19]
Vollheim et al.

[11] 3,941,717
[45] Mar. 2, 1976

[54] PROCESS FOR THE PRODUCTION OF A CATALYST COMPRISING A NOVEL METAL ON ACTIVATED CARBON

[75] Inventors: Gerhard Vollheim, Hanau; Karl-Jurgen Troger, Grossauheim; Gerhard Lippert, Kleinostheim, all of Germany

[73] Assignee: Deutsche Gold- und Silber-Scheideanstalt vormals Roessler, Germany

[22] Filed: Sept. 27, 1972

[21] Appl. No.: 292,797

[30] Foreign Application Priority Data
Oct. 8, 1971   Germany.............................. 2150200

[52] U.S. Cl. ................ 252/430; 252/439; 252/447; 260/580
[51] Int. Cl.² ......................................... B01J 21/18
[58] Field of Search..................... 252/447, 439, 430

[56] References Cited
UNITED STATES PATENTS

| | | | |
|---|---|---|---|
| 2,285,277 | 6/1942 | Henke et al. ....................... | 252/447 |
| 2,823,235 | 2/1958 | Graham et al. .................. | 252/447 X |
| 3,328,465 | 6/1967 | Spiegler .......................... | 252/447 X |
| 3,736,266 | 5/1973 | Schrage ............................. | 252/447 |

*Primary Examiner*—Patrick P. Garvin
*Attorney, Agent, or Firm*—Cushman, Darby & Cushman

[57] ABSTRACT

Catalysts of noble metals on activated carbon are subjected to the action of a sulfoxide together with hydrazine or its derivatives. The catalysts are particularly useful in the selective hydrogenation of chloronitroaromatic compounds.

19 Claims, No Drawings

PROCESS FOR THE PRODUCTION OF A CATALYST COMPRISING A NOVEL METAL ON ACTIVATED CARBON

The invention is directed to a process for the production of a catalyst containing a noble metal on activated carbon. The catalyst is suitable for use in the selective hydrogenation of chloronitro-aromatic compounds.

The suitability of catalysts for the hydrogenation of chloronitro-aromatic compounds depends on their selectivity and activity. With normal platinum-activated carbon catalyst this reaction can only be carried out poorly when selecting milder reaction conditions because of the hydrogen chloride splitting off in a side reaction. The platinum-activated carbon catalyst can be sulfidized for example with hydrogen sulfide and its salts or polysulfides (German Patent No. 1,260,444 and German Offenlegungschrift 1,959,578). The yields of chloro-amino-aromatic compounds obtained by hydrogenation of chloronitro-aromatic compounds with such catalysts are 95–98%. The reaction time is less than one hour. However, a relatively large amount of catalyst is required for example corresponding to a ratio of platinum : substrate of 1 : 1,560.

It is also known from the Annals New York Academy of Sciences Vol. 145 (1), pages 31–45(1967) to use sulfoxide to influence the selectivity.

The invention is based on the problem of providing a catalyst for the hydrogenation of chloronitro-aromatic compounds which at an at least as good activity permits the obtaining of a better selectivity.

It has now been found surprisingly that this goal can be attained with a catalyst which is prepared by subjecting a noble metal-activated carbon catalyst to the action of a sulfoxide and then to hydrazine or its derivatives.

As starting materials there can be used noble metal-activated carbon catalysts produced in known manner. Thus there can be used catalysts of platinum, palladium, rhodium, iridium or rhenium or their mixtures, e.g. platinum-rhodium, on activated carbon. According to a preferred form of the process there are used as starting materials platinum or palladium-activated carbon catalysts. These have proven especially suitable.

In the process there can be added all kinds of sulfoxides, for example alkyl, aryl and aralkyl sulfoxides such as dimethyl sulfoxide, diethyl sulfoxide, di n-propyl sulfoxide, di n-butyl sulfoxide, diisoamyl sulfoxide, benzyl phenyl sulfoxide, diphenyl sulfoxide, methyl phenyl sulfoxide, dibenzyl sulfoxide, di p-tolyl sulfoxide. Expecially suitable is dimethyl sulfoxide.

The hydrazine treatment in the second step produces in an unexpected manner an observable increase in the catalyst activity. In the realm of the invention process all kinds of hydrazine compounds can be added. Thus there can be used in place of hydrazine, alkyl, alkenyl, aralkyl and aryl hydrazine such as methyl hydrazine, ethyl hydrazine, allyl hydrazine, isopropyl hydrazine, cyclohexyl hydrazine, n-hexadecyl hydrazine, benzyl hydrazine, phenyl hydrazine, p-tolyl hydrazine, and 2-naphthyl hydrazine. Normally there is used unsubstituted hydrazine hydrate.

The outstanding selectivity of the catalysts modified according to the invention can be seen from the following comparison. In the hydrogenation of 2-chloronitrobenzene with the use of a dimethyl sulfoxide treated platinum-activated carbon catalyst there were obtained a yield of 98.4% of 2-chloroamino benzene. In contrast using a platinum-activated carbon catalyst which was treated according to the invention in a first step with dimethyl sulfoxide and in a second step with aqueous hydrazine hydrate solution there was obtained reproducibly a yield of 99.6% of 2-chloroaminobenzene.

Palladium-activated carbon catalysts modified according to the invention give yields of about 98%. Palladium catalysts are less selective then platinum catalysts in the hydrogenation of chloronitro aromatic compounds. In view of the lower basic costs of palladium-activated carbon catalysts it is a great advantage that using such palladium-activated carbon catalysts there can be obtained the optimum yields that are set forth for sulfidized platinum catalysts in German Offenlegungsschrift 1,959,578. This was not to be expected. Advantageously the sulfoxide and hydrazine treating agents are preferably added as solutions, especially in water. The strength of such solutions is not critical. The starting noble metal-activated carbon catalyst can either be modified with the liquid treating agents (sulfoxide and hydrazine) or their solutions of the treating agents or vapors of the treating agent. The amount of treating agent is not critical, thus for example the sulfoxide can be used in an amount of 0.1 to 10 moles per mole of noble metal and the hydrazine compound can be used, for example, in an amount of 0.1 to 10 moles per mole of noble metal.

In regard to their selectivity especially suitable catalysts are obtained if an aqueous suspension of the starting noble metal-activated carbon catalyst is treated with aqueous dimethyl sulfoxide, after 10 minutes stirring 24% aqueous hydrazine hydrate solution is added, then stirring is again carried out for 10 minutes and subsequently hydrogenation can take place.

Both treating steps can be carried out at the same temperatures. A wide range of temperatures can be used in the process. Mild conditions are preferred. In working in the aqueous phase with dimethyl sulfoxide and hydrazine hydrate for example as the modifying agent, good results are produced in the temperature range of 50° to 80°C. However, as stated the temperature is not critical, e.g. room temperature can be used.

Unless otherwise indicated all parts and percentages are by weight.

The catalysts of the invention can be used to hydrogenate chloronitro-aromatic compounds to the corresponding chloroamino aromatic compounds, e.g. 2-chloronitrobenzene, 3-chloronitrobenzene, 4-chloronitrobenzene, 3-chloro-4-methyl nitrobenzene, 3,5-dichloronitrobenzene, 1-chloro-2,4-dinitrobenzene, 3-chloro-5-ethyl nitrobenzene.

The invention will be further explained by the following examples in which the production of catalysts is shown in examples 1 to 3 and the catalysts produced are added in the hydrogenation of chloronitro aromatic compounds in examples 4 to 7.

In examples 4 to 7 there was always used a pressure of 10 atmospheres absolute and a maximum temperature of 105°C. However, it is also possible to operate at higher pressures and temperatures although, based on principle, the mildest possible conditions are strived for. The use of sulfoxides therefore is of especial significance since they can be unhesitatingly be handled in contrast to the poisonous sulfides.

EXAMPLE 1

100 grams of platinum-activated carbon catalyst (F 103 R of Degussa) having a platinum content of 1% were suspended in 400 ml of water and heated to 60°C. After addition of 1 gram of dimethyl sulfoxide the mixture was stirred further for 15 minutes at 60°C. The catalyst was then filtered with suction and washed. It can be added in the wet condition.

EXAMPLE 2

100 grams of the same platinum-activated carbon catalyst used in Example 1 (1% platinum on activated carbon) were suspended in 400 ml of water and heated to 60°C. Then there was added 1 gram of dimethyl sulfoxide. After stirring for 10 minutes it was treated with 2 ml of a 24% aqueous hydrazine hydrate solution. After 10 minutes further of stirring at 60°C. it was filtered with suction and washed with water.

EXAMPLE 3

100 grams of catalyst E 10 R of Degussa (5% palladium on activated carbon) were suspended with stirring in 400 ml of water and heated to 60°C. Then there were added 4 grams of dimethyl sulfoxide. After 10 minutes stirring it was treated with 8 ml of 24% aqueous hydrazine hydrate. After a further 10 minutes stirring at 70°C. the product was filtered with suction and washed with water.

EXAMPLE 4

160 grams of 2-chloronitrobenzene was hydrogenated in a Hofer autoclave (capacity ½ liter) at a constant pressure of 10 atmospheres absolute without a solvent. 2 grams of moist catalyst produced according to Example 1 and having a 50% dry material content was added. The amount of platinum was 1/16,000 of the amount of substrate. The hydrogenation took 146 minutes at 90°C. There were obtained by gas chromatographic analysis 98.4% of the theoretical chloroaniline yield.

EXAMPLE 5

The catalyst of Example 2 was employed under identical conditions with Example 4. At 90°C, inside of 157 minutes there was obtained a yield of 99.6% of chloroaniline.

EXAMPLE 6

There was used in this case also the catalyst of Example 2 and using the conditions of Example 4. However, the chloronitroaromatic compound employed was 3-chloro-4-methyl-nitrobenzene. The temperature amounted to 105°C., the reaction time was 105 minutes. The yield of 3-chloro-4-methyl aniline was 99.8%.

EXAMPLE 7

The catalyst of Example 3 was employed in the hydrogenation of 2-chloronitrobenzene, again under the conditions of Example 4. There were added, based on the dry material, 0.5 grams of catalyst (ratio of substrate : palladium was 6400 : 1). The hydrogenation temperature was 80°C. In the space of 185 minutes there was obtained a yield of 98%.

The amount of noble metal on the activated carbon can be that conventionally employed, e.g., 1 to 10%.

What is claimed is:

1. A process for the production of a catalyst of a noble metal on activated carbon suitable for the selective hydrogenation of chloronitro-aromatic compounds comprising treating the noble metal-activated carbon with a sulfoxide of the formula $R_1SOR_2$ where $R_1$ and $R_2$ are alkyl, aralkyl or aryl and then with a hydrazine material having the formula $R_3NHNH_2$ where $R_3$ is hydrogen, alkyl, aryl, aralkyl or alkenyl.

2. The process according to claim 1 wherein the noble metal is platinum or palladium.

3. A process according to claim 2 wherein the noble metal is platinum.

4. A process according to claim 2 wherein the noble metal is palladium.

5. A process according to claim 2 wherein the sulfoxide is dimethyl sulfoxide.

6. A process according to claim 5 wherein the hydrazine material is hydrazine in the form of hydrazine hydrate.

7. A process according to claim 2 wherein the hydrazine material is hydrazine in the form of hydrazine hydrate.

8. A process according to claim 2 wherein an aqueous suspension of the noble metal-activated carbon catalyst is first treated with aqueous dimethyl sulfoxide, stirred for 10 minutes, 24% aqueous hydrazine hydrate solution is then added, stirring is again carried out for 10 minutes and the product filtered.

9. The product produced by the process of claim 2.

10. The product produced by the process of claim 1.

11. A process according to claim 1 wherein the sulfoxide is dimethyl sulfoxide, diethyl sulfoxide, di-n-propyl sulfoxide di-n-butyl sulfoxide, diisoamyl sulfoxide, benzyl phenyl sulfoxide, diphenyl sulfoxide, methyl phenyl sulfoxide, dibenzyl sulfoxide, or di-p-tolyl sulfoxide and the hydrazine material is hydrazine, methyl hydrazine, ethyl hydrazine, allyl hydrazine, isopropyl hydrazine, cyclohexyl hydrazine, n-hexadecyl hydrazine, benzyl hydrazine, phenyl hydrazine, p-tolyl hydrazine or 2-naphthyl hydrazine.

12. A process according to claim 1 wherein both the sulfoxide and the hydrazine material are employed as solutions in water.

13. A process for the production of a catalyst of a noble metal on activated carbon consisting essentially of the treatment set forth in claim 1.

14. A process according to claim 13 wherein both the sulfoxide and the hydrazine material are employed as solutions in water.

15. A process according to claim 14 wherein there is used 0.1 to 10 moles of sulfoxide and 0.1 to 10 moles of hydrazine material per mole of noble metal.

16. A process according to claim 13 wherein there is used 0.1 to 10 moles of sulfoxide and 0.1 to 10 moles of hydrazine material per mole of noble metal.

17. A process according to claim 15 including the steps of filtering and washing the product.

18. A process according to claim 1 wherein the two steps of the treatment are carried out at room temperature to 80°C.

19. A process for the production of a catalyst of a noble metal on activated carbon suitable for the selective hydrogenation of chloronitro aromatic compounds consisting essentially of treating the noble metal-activated carbon with a sulfoxide of the formula $R_1SOR_2$ where $R_1$ and $R_2$ are alkyl, aralkyl or aryl and then with a hydrazine material having the formula $R_3NHNH_2$ where $R_3$ is hydrogen, alkyl, aryl, aralkyl or alkenyl, the two steps of said treatment being carried out at 50°–80°C and using 0.1 to 10 moles of sulfoxide and 0.1 to 10 moles of hydrazine material per mole of noble metal.

* * * * *

UNITED STATES PATENT OFFICE
CERTIFICATE OF CORRECTION

Patent No. 3,941,717  Dated March 2, 1976

Inventor(s) Gerhard Vollheim, Karl-Jürgen Tröger, Gerhard Lippert

It is certified that error appears in the above-identified patent and that said Letters Patent are hereby corrected as shown below:

Change Item [30] as follows:

--[30] Foreign Application Priority Data

Oct. 8, 1971   Germany......... 2150220.5--

Signed and Sealed this

Fourteenth Day of September 1976

[SEAL]

Attest:

RUTH C. MASON
*Attesting Officer*

C. MARSHALL DANN
*Commissioner of Patents and Trademarks*